United States Patent [19]

Van Rheenen et al.

[11] Patent Number: 4,526,720
[45] Date of Patent: Jul. 2, 1985

[54] PROCESS TO PREPARE STABILIZED MONOLITHIUM ACETYLIDE

[75] Inventors: Verlan H. Van Rheenen, Portage; Dae Y. Cha, Kalamazoo, both of Mich.

[73] Assignee: The Upjohn Company, Kalamazoo, Mich.

[21] Appl. No.: 568,558

[22] Filed: Jan. 5, 1984

[51] Int. Cl.$^3$ .................................. C07J 1/00
[52] U.S. Cl. ...................... 260/397.4; 260/397.45; 260/397.5; 260/665 R
[58] Field of Search ............. 260/397.4, 397.5, 665 R, 260/397.45

[56] References Cited

U.S. PATENT DOCUMENTS 4,055,562 10/1977 Christiansen .................... 260/397.4

OTHER PUBLICATIONS

Midland; "Journal of Organic Chemistry," vol. 40, No. 15, (1975), pp. 2250–2252.
J. Chem. Soc. 4765, (1956), "Researches on Acetylenic Compounds, Part LIV, The Preparation and Synthetical . . . ", by Jones, Skattebol and Whiting.
J. Mol. Structure 42, 251, (1977), by Moffat, "Linear Alkynes and the Effect on Bond Lengths of Chain . . . ".
J. Am. Chem. Soc. 98, 4778, (1976), by Streitwieser, "Ab Initio SCF–MO Calculations of Methyllithium and Related Systems . . . ".
Fieser & Fiester, Steroids, Reinhold Publishing Co., N.Y., 1959, pp. 557–591.
J. Am. Chem. Soc. 78, 2477, (1956), "Steroids . . . ", by H. J. Ringold et al.
J. Org. Chem. 34, 435, (1969), "Liquid Acetylene . . . ", by R. J. Tedeschi and G. L. Moore.
J. Org. Chem. 40, 2250, (1975), by Midland, "Preparation of Monolithium Acetylide in Tetrahydrofuran . . . ".
Chim. Ind. (Milan) 42, 251, (1960), M. Corbellini; L. Turner.
Chem. Abstr. 54, 19250, (1960).

*Primary Examiner*—Elbert L. Roberts
*Attorney, Agent, or Firm*—Bruce Stein

[57] ABSTRACT

The process of the present invention uses an amine to prepare monolithium acetylide which is sufficiently stable at up to 0° and yet is sufficiently reactive to react with 16-substituted-17-keto steroids producing the useful 17α-ethynyl-17β-hydroxy-16-substituted steroids.

17 Claims, No Drawings

PROCESS TO PREPARE STABILIZED MONOLITHIUM ACETYLIDE

DESCRIPTION

BACKGROUND OF THE INVENTION

Ethynylation of 17-keto steroids to produce commercially important 17α-ethynyl-17β-hydroxy steroids is well known to those skilled in the art. See, for example, U.S. Pat. Nos. 2,272,131, 2,843,609, 2,723,280, 2,877,240, 4,041,055, Steroids by Fieser and Fieser, Reinhold Publishing Co., New York, 1959, pp. 557–591, and J. Am. Chem. Soc. 78, 2477 (1956).

The general method of ethynylation is to react the 17-keto steroid with dipotassium acetylide. The advantage of the dipotassium acetylide process is that it can be used with $\Delta^4$-3-keto steroids without having to protect the 3-keto group. However, that procedure cannot be used with 16α-methyl-17-keto, 16β-methyl-17-keto or 16-methyl-17-keto steroids for well known reasons. Commercially the ethynylation of 16α- or 16β-methyl- as well as 16-methylene-17-keto steroids is important because the 17α-ethynyl-17β-hydroxy-16α-methyl, 17α-ethynyl-17β-hydroxy-16β-methyl and 17α-ethynyl-17β-hydroxy-16-methylene steroids can be transformed to dexamethasone, betamethasone and melengestrol acetate.

Metallo-acetylides other than dipotassium acetylide are known. Monosodium acetylide is known, see R. J. Tedeschi, et al., J. Org. Chem. 34, 435 (1969). Mono- and bis-magnesium acetylides are known, see L. Skattebol, et al., J. Chem. Soc. 4765 (1956). Although the use of magnesio-acetylides has been reported for 17α-ethynyl introduction, substantial dimer formation results with both mono- and bis-magnesioacetylides, see U.S. Pat. No. 3,704,253.

Lithioacetylide reagents exhibit substantially different reactivity in many cases from other metallo-acetylides. This fact and the ready availability of n-butyllithium has resulted in the extensive use of these reagents in syntheses. The covalent nature of the carbon-lithium bond has been the subject of many theoretical and experimental investigations, see, for example, J. B. Moffat, J. Mol. Structure 42, 251 (1977) and A. Streitwieser, et al., J. Am. Chem. Soc. 98, 4778 (1976).

M. M. Midland in J. Org. Chem. 40, 2250 (1975) reported reacting n-butyllithium with acetylene in THF at low temperature ($<-70°$) and in dilute solution to produce monolithium acetylide. Monolithium acetylide is a valuable reagent for the preparation of ethynyl carbinols and terminal acetylenes, see Fieser and Fieser, Reagents for Organic Synthesis, Vol. 1, Wiley, New York, 1967, p 573. Midland found that warming or attempting to generate a more concentrated solution resulted in disproportionation to the insoluble dilithium acetylide and acetylene. This disproportionation is an important disadvantage and occurs in the absence of a complexing agent, see Corbellini et al., Chem. Ind. (Milan) 42, 251 (1960) and Chem Abstr. 54, 19250 (1960). To reduce or prevent the disproportionation the monolithium acetylide is usually prepared in liquid ammonia, which presumably serves as an appropriate complexing agent. An amine such as ethylenediamine can also be used to stabilize monolithium acetylide. Ethylenediamine so greatly stabilizes monolithium acetylide that monolithium acetylide is sold commercially as an ethylenediamine complex. Ethylenediamine while stabilizing monolithium acetylide to the point it can be sold commercially actually reduces the reactivity to the point it is not useful for many ethynylation procedures.

U.S. Pat. No. 4,055,562 used monolithium acetylide to ethynylate 17-keto steroids unsubstituted in the $C_{16}$ position. The monolithium acetylide was prepared by bubbling acetylene into THF held at $-70°$ under anhydrous conditions followed by addition of butyllithium. The 17-keto steroid was added to the unstabilized monolithium acetylide and the mixture stirred for 3 hr at $-70°$ to produce the 17α-ethynyl-17β-hydroxy steroid product.

U.S. Pat. No. 4,320,236 discloses the use of a monolithium acetylideammonium complex (which is well known to those skilled in the art) to ethynylate ketones at below about 30°. The examples in U.S. Pat. No. 4,320,236 disclose ethynylation reaction temperatures of $-50°$ to 10°. The unsaturated acyclic ketones ethynylated in U.S. Pat. No. 4,320,236 are very reactive whereas the monolithium acetylide produced by the process of the present invention is reactive with steroidal 17-ketones which are highly substituted sterically hindered cyclopentanones and therefore much less reactive.

The process of the present invention produces stabilized monolithium acetylide which can be prepared and reacted at up to 0° and yet which is sufficiently reactive to react with 16α- and 16β-methyl- and 16-methylene-17-keto steroids to produce the desired 16-substituted-17α-ethynyl-17β-hydroxy steroids in very high yields.

SUMMARY OF THE INVENTION

Disclosed is a two pot process to prepare monolithium acetylide which comprises (1) dissolving acetylene in a dry solvent, (2) contacting a stabilizing amine with an organo-lithium compound at about 0° or less and (3) contacting the product of step (2) with the solution of step (1) at about 0° or less.

Also disclosed is a one pot process to prepare monolithium acetylide which comprises (1) dissolving acetylene in a dry solvent, (2) contacting a stabilizing amine with the solution of step (1) and (3) contacting an organo-lithium compound with the mixture of step (2) at about 0° or less.

Further disclosed is an in situ process to prepare monolithium acetylide which comprises (1) dissolving acetylene in a dry solvent; (2) contacting a 17-keto steroid with the mixture of step (1), (3) contacting a stabilizing amine with an organo-lithium compound at about 0° or less and (4) contacting the mixture of step (3) with the carbonyl-acetylene mixture of step (2) at about 0° or less.

DETAILED DESCRIPTION OF THE INVENTION

The process of the present invention to prepare a stabilized monolithium acetylide can be practiced in 3 alternative ways, two pot (preferred), one pot or in situ.

In the two pot process, a sufficient quantity of acetylene is first dissolved in a suitable dry organic solvent. The temperature at which the acetylene can be dissolved in the dry organic solvent is not critical. The temperature affects the solubility and therefore the concentration of the acetylene. However, before the acetylene solution is contacted with the lithium complex it must be cooled to 0° or less. The nature of the organic solvent is not critical so long as it does not react with acetylene, organolithium compounds or amines. Suitable dry organic solvents include THF, dioxane, diethyl ether, t-butyl methyl ether and dimethoxyethane. The preferred solvent is THF. It is convenient for the organic solvent to be saturated with acetylene. Second, an organo-lithium compound is contacted with a stabilizing amine at 0° or less in a suitable dry organic solvent. Organo-lithium compounds include n-butyllithium, phenyllithium, and methyllithium, preferred is n-butyllithium. A stabilizing amine is an amine (primary, secondary or tertiary) which when reacted with an organo-lithium compound to form a lithium complex and/or corresponding lithium amine subsequently reacted with acetylene forms a stabilized monolithium acetylide which will not significantly disproportionate at 0° and below which is reactive towards 17-keto steroids. Stabilizing amines include N,N-diisopropyl ethyl amine, triethylamine, diisopropyl amine, t-butyl amine, diethylamine, dicyclohexylamine; hexamethyl disilazane, and pyrrolidine. Some amines such as pyrrolidine are only useful with some steroids such as 16$\beta$-methylandrosta-1,4,9(11)-triene-3,17-dione. Amines which are not operable include ethylenediamine and pyridine. Preferred is diisopropylamine. The same dry organic solvents useful to dissolve the acetylene in are also useful here. It is preferred that the same solvent or mixture of solvents be used for dissolving the acetylene in as for the reaction of the organo-lithium compound with the stabilizing amine. The reaction of the organo-lithium compound with a primary or secondary amine produces a lithium amide. A tertiary amine cannot produce a lithium amide and forms a complex, the nature of which is not known. Therefore, the reaction of an organo-lithium compound and a stabilizing amine will be considered to have produced a lithium complex. When the organo-lithium compound is added to the stabilizing amine it must be added slowly maintaining the temperature at about 25° or less. The reaction is complete in less than 30 min.

The third step of the two pot process is contacting the lithium complex of step 2 with the acetylene solution of step 1 at 0° or less. It is preferred that the method of contacting be a slow addition of the lithium complex to the acetylene solution keeping the temperature at 0° or less. The reaction forming monolithium acetylide is complete in about 30 min.

In the two pot process, the first two steps which are independent of each other can be performed in the reverse order. The organo-lithium compound can be reacted with the stabilizing amine prior to the dissolving of the acetylene in the dry organic solvent. All that is necessary is that both steps be independently performed and the temperature of both mixtures be 0° or less before they are combined in the third step.

The 17-keto steroid to be ethynylated is added to the monolithium acetylide at 0° or less. The ethynylation reaction is complete in about 30 minutes. The 17-keto steroid can be added as a solid, a slurry or as a solution. For convenience it is preferred that it be added as a solution. It should be added slowly as is known to those skilled in the art. Again, the same organic solvents used for steps 1 and 2 are useful for adding the material to be ethynylated to the monolithium acetylide. Again, it is preferable to use the same organic solvent as was used in steps 1 and 2. The ethynylated product is recovered by means well known to those skilled in the art.

In the one pot process, the first step of dissolving the acetylene in a suitable dry organic solvent is the same as for the two pot process. Second, the stabilizing amine is added to the acetylene solution at 0° or less. Third, the organo-lithium compound is added slowly to the mixture of the acetylene solution and the stabilizing amine again at 0° or less.

With the in situ process, the first step again is the same. Second, the 17-keto steroid to be ethynylated is added to the acetylene solution at 0° or less. Third, the organo-lithium compound and the stabilizing amine are reacted to form the lithium complex as in the second step of the two pot process. Finally, the lithium complex is added slowly to the mixture of the acetylene solution containing the 17-keto steroid to be ethynylated at 0° or less and the monolithium acetylide is generated in situ.

While the above steps can be performed at 0° it is preferable to perform them at less than −20°, more preferable in a temperature range of about −20° to about −40°. Reducing the temperature reduces the amount of disproportionation, thereby increasing the amount of monolithium acetylide available for ethynylation.

The stabilized monolithium acetylide produced by the process of the present invention is reactive with aldehydes and ketones. It is preferred that the reactant be a 17-keto steroid. Commercially one of the most important uses of the ethynylation process is the transformation of 17-keto steroids to the corresponding 17$\alpha$-ethynyl-17$\beta$-hydroxy steroid. For example, androstenedione, a 17-keto steroid (protected as the 3-enol ether) is ethynylated to ethisterone (Example 1). Ethisterone by the process of U.S. Pat. No. 4,041,055 (Examples 1, 5, 9 and 13) is converted to 17$\alpha$-hydroxyprogesterone. Androstenedione is a $\Delta^4$-3-keto steroid and can be ethynylated with dipotassium acetylide (preferably) or monolithium acetylide. In Preparation 1 of U.S. Pat. No. 4,041,055 monolithium acetylide ethylene diamine was used, it is sufficiently reactive to react with androstenedione which has no substitution at $C_{16}$ but is not sufficiently reactive to react with 16-substituted-17-keto steroids such as 16$\alpha$-methyl-, 16$\beta$-methyl- or 16-methylene-17-keto steroids without serious side reactions.

The monolithium acetylide produced by the process of the present invention is sufficiently stable at up to about 0° and is reactive with 16$\alpha$-methyl-, 16$\beta$-methyl and 16-methylene-17-keto steroids. 16$\alpha$-methyl- and 16$\beta$-methyl-17-keto steroids are well known to those skilled in the art. 16-Methylene-17-keto steroids are also known, see for example U.S. Pat. No. 4,416,821.

The 17$\alpha$-ethynyl-17$\beta$-hydroxy-16-methyl steroids are useful as intermediates in the preparation of 16-methyl-17$\alpha$-hydroxyprogesterones and 16-methyl corticoids, see U.S. Pat. No. 4,041,055. For example, 17$\alpha$-ethynyl-17$\beta$-hydroxy-16$\beta$-methylandrosta-1,4,9(11)-trien-3-one (Example 2) is transformed to 17$\alpha$,21-dihydroxy-16$\beta$-methylpregna-1,4,9(11)-triene-3,20-dione by the process of U.S. Pat. No. 4,041,055. This $\Delta^{9(11)}$-corticoid is transformed by known methods to the bromohydrin, 9$\beta$,11$\beta$-epoxide and finally to the corresponding 9$\alpha$-fluoro-11$\beta$-hydroxy compound which is betamethasone (U.S. Pat. No. 3,485,854).

16-Methylene-17-keto steroids are known, see U.S. Pat. Nos. 3,300,521, 3,641,069, and 4,416,821, Gazz. Chim. Ital. 91, 972 (1961), and Hungarian Pat. No. 019,495. The 16-methylene-17-keto steroids can be efficiently ethynylated with the stabilized monolithium acetylide produced by the process of the present invention to give 17$\alpha$-ethynyl-17$\beta$-hydroxy-16-methylene steroids, see Examples 3 and 4.

The 17α-ethynyl-17β-hydroxy-16-methylene steroids are useful intermediates in the preparation of 17α-hydroxy-16-methylene-progesterones, see Chart A. The 17α-ethynyl-17β-hydroxy-16-methylene steroid is transformed to the corresponding 17β-hydroxy steroid by reaction with a mercuric agent. Oxymercuration of ethisterone derivatives is old, see Helv. Chim. Acta. 26, 680 (1943). However, the present D ring is not a simple ethisterone derivative. Here the 17α-ethynyl-17β-hydroxy substituents are allylic to a 16-methylene group. Surprisingly and unexpectedly quantitative yields of the 17β-hydroxy steroids are obtained indicating that its allylic alcohol system did not compete with the propargyl alcohol system in the oxymercuration.

The mercuric agent can be produced by reaction of mercuric oxide with a strong acid such as sulfuric, hydrochloric, or nitric acid. The mercuric salts, mercuric sulfate, mercuric chloride or mercuric nitrate can be used directly in acid medium. Mercuric sulfate or this salt made from mercuric oxide and sulfuric acid is preferred. A catalytic amount of a mercuric agent and the 17α-ethynyl-17β-hydroxy-16-methylene steroid are contacted at 20°–65° for 2–24 hr in an aqueous polar solvent. When the oxymercuration reaction is complete, the reaction mixture is filtered (thru Celite) to remove insoluble mercuric salt solids and the 17β-hydroxy steroid is recovered from the filtrate by means well known to those skilled in the art. Alternatively the oxymercuration reaction can be performed using the mercuric agent affixed to a resin. See M. S. Newman, J. Am. Chem. Soc., 75, 4740 (1953).

The 17β-hydroxy steroids are next converted to the corresponding sulfoxides by reaction with a sulfenylating agent of the formula $R_{22}$-S-M. It is preferred that M is a chlorine or bromine atom, more preferred that M be a chlorine atom. It is preferred that $R_{22}$ be methyl, phenyl, p-chlorophenyl, p-methoxyphenyl or p-methylphenyl. It is more preferred that $R_{22}$ be phenyl.

The appropriately substituted sulfenylating agents are prepared by methods known to those skilled in the art. For example, sulfuryl chloride is added to a thiol previously dissolved in an organic solvent such as methylene chloride. See Chem. Reviews, 39, 269 (1946) at page 279 and U.S. Pat. No. 2,929,820.

The sulfenylation reaction is carried out in a nonpolar aprotic solvents such as toluene, chloroform, diethyl ether, or methylene chloride, THF, and dioxane or mixtures thereof. It is preferred that the solvent be methylene chloride. The reaction is carried out in the presence of at least an equal molar amount of a tertiary amine base, such as triethylamine, trimethylamine or pyridine. Trimethylamine is preferred. Any excess base serves as additional solvent for the reaction. The reaction is preferably carried out under an inert dry gas such as nitrogen, argon, or carbon dioxide. The substituted sulfenyl halide is added dropwise to the reaction mixture at a temperature of −20° to −40°. Following addition of the substituted sulfenylating agent to the reaction mixture, the excess substituted sulfenylating agent is quenched with an appropriate quenching agent such as water, cyclohexene, various alcohols such as methanol and ethanol, or acetone. The sulfoxide may be obtained by standard workup.

The sulfoxide exists as 2 double bond isomers; where the unsaturation is between $C_{16}$ and the carbon atom attached to the sulfur atom. The endocyclic isomer usually predominates with only small amounts of the exocyclic isomer. However, the ratio of the isomeric sulfoxides is unimportant for the purposes of the present invention as both isomers are converted to the same product in the next step.

The sulfoxides are converted to the corresponding 16-methylene-17α-hydroxyprogesterones by reaction with a thiophile with heat. The sulfoxides are placed in an appropriate solvent or mixture of solvents such as toluene, methanol, ethylene dichloride or acetone. Some thiophiles such as hydroxide, alkoxide, etc. produce undesirable side reactions; others such as trimethylphosphite and diethylamine and mixtures thereof are more suitable. The preferred thiophile is trimethylphosphite. Trimethylphosphite is known as a thiophile, see D. A. Evans & G. C. Andrews, Acct. of Chem. Res. 7, 147 (1974) at p. 150. The sulfoxide and thiophile are contacted and heated from about 50°–100° depending on solvent(s), sulfoxide, thiophile, and whether or not the reaction is conducted under pressure. It is preferred to heat the reaction mixture from 60°–90° in a sealed reacting container for 4–24 hr. When the reaction is complete the 16-methylene-17α-hydroxyprogesterone is isolated and purified by means well known to those skilled in the art.

The 16-methylene-17α-hydroxyprogesterones are useful as intermediates in the production of commercial pharmaceutical agents in two ways. First, 16-methylene steroids are intermediates in the manufacture of certain progestational agents such as melengestrol acetate, and second where the 16-methylene group is reduced to 16α-methyl or 16β-methyl to give intermediates useful in the production of antiinflammatory corticoids. For example, androstenedione can be converted to melengestrol acetate, a 16-methylene steroid in the following manner: (1) androstenedione is converted to 6-methyleneandrost-4-ene-3,17-dione by the process of U.S. Pat. No. 3,642,840, Example 18; (2) 6-methyleneandrost-4-ene-3,17-dione is converted to 6-methylandrosta-4,6-diene-3,17-dione by the process of U.S. Pat. No. 3,117,966, Example 16; (3) 6-methylandrosta-4,6-diene-3,17-dione is converted to 6-methyl-16-methyleneandrosta-4,6-diene-3,17-dione by the process of U.S. Pat. No. 4,416,821; (4) 6-methyl-16-methyleneandrosta-4,6-diene-3,17-dione is converted to 17α-ethynyl-17β-hydroxy-6-methyl-16-methyleneandrosta-4,6-dien-3-one by the process of the present invention, which is converted to 17α-hydroxy-6-methyl-16-methylenepregna-4,6-diene-3,20-dione as described above; and (5) acylation of the 17α-hydroxy-6-methyl-16-methylenepregna-4,6-diene-3,20-dione to 17-acetyloxy-6-methyl-16-methylenepregna-4,6-diene-3,20-dione (melengestrol acetate) by the process of U.S. Pat. No. 4,154,748, Example 12.

Alternatively, and preferably, the following sequence can be used: (1) 16-methylene androstenedione (Hungarian Pat. No. 019,495, Example 3) is converted to 17α-ethynyl-3,17β-dihydroxy-16-methyleneandrosta-3,5-diene 3-methyl ether by the process of the present invention, then (2) the 17α-ethynyl-3,17β-dihydroxy-16-methyleneandrosta-3,5-diene 3-methyl ether is converted to 17α-ethynyl-17β-hydroxy-6,16-dimethyleneandrost-4-en-3-one by the process of U.S. Pat. No. 3,642,840, (3) the 17α-ethynyl-17β-hydroxy-6,16-dimethyleneandrost-4-en-3-one is then converted to the corresponding 17β-hydroxy steroid, sulfoxide and ultimately to 17α-hydroxy-6,16-dimethylenepregn-4-ene-3,20-dione, which upon reaction with acetic anhydride and p-TSA forms 17α-acetyloxy-6-methyl-16- methylenepregna-4,6-diene-3,20-dione, melengestrol acetate.

The 16-methylene-17α-hydroxyprogesterones can readily be transformed into a 16-methylene corticoid by reaction with iodine, an excess of calcium oxide, an aqueous sodium hydroxide and potassium acetate in acetone as is well known, see for example H. J. Ringold, et al., J. Am. Chem. Soc. 80, 250 (1958), O. Halpern, et al., J. Am. Chem. Soc. 81, 439 (1959) and J. Org. Chem. 25, 1060 (1966). The 16-methylene corticoid can then be readily transformed to a 16β-methyl corticoid by the process of U.S. Pat. No. 3,115,508 or to a 16α-methyl corticoid by the process of U.S. Pat. No. 3,130,209.

For example, betamethasone (9α-fluoro-11β,17α,21-trihydroxy-16β-methylpregna-1,4-diene-3,20-dione) can be prepared from 17β-hydroxy-16-methylenepregna-1,4,9(11)-triene-3,20-dione by first transforming it to 17α,21-dihydroxy-16-methylenepregna-1,4,9(11)-triene-3,20-dione 21-acetate by the process of J. Am. Chem. Soc. 80, 250 (1958), J. Am. Chem. Soc. 81, 439 (1959) and J. Org. Chem. 25, 1966 (1960) and next transforming it to 17α,12-dihydroxy-16β-methylpregna-1,4,9(11)-triene-3,20-dione 21-acetate by the process of U.S. Pat. No. 3,115,508. The transformation of 17α,21-dihydroxy-16β-methylpregna-1,4,9(11)-triene-3,20-dione 21-acetate to betamethasone is described in U.S. Pat. No. 3,104,246, Examples I and II.

Dexamethasone (9α-fluoro-11β,17α,21-trihydroxy-16α-methylpregna-1,4-diene-3,20-dione) can also be prepared from 17β-hydroxy-16-methylenepregna-1,4,9(11)-triene-3,20-dione by first transforming it to 17α,21-dihydroxy-16-methylenepregna-1,4,9(11)-triene-3,20-dione 21-acetate as described above and next transforming it to 17α,21-dihydroxy-16α-methylpregna-1,4,9(11)-triene-3,20-dione 21-acetate by the process of U.S. Pat. No. 3,130,209. 17α,21-Dihydroxy-16α-methylpregna-1,4,9(11)-triene-3,20-dione 21-acetate is then epoxidized by means well known to those skilled in the art, see for example U.S. Pat. No. 3,980,778, Examples 2 and 7 to produce 9β,11β-epoxy-17α,21-dihydroxy-16α-methylpregna-1,4-diene-3,20-dione which is transformed to dexamethasone 21-acetate by the process of U.S. Pat. No. 3,007,932, Example 2.

Likewise diflorasone diacetate (6α,9α-difluoro-11β,17α,21-trihydroxy-16β-methylpregna-1,4-diene-3,20-dione 17,21-diacetate, U.S. Pat. No. 3,980,778) can be produced using the process of the present invention. First, 6α-fluoro-11β-hydroxyandrosta-1,4-diene-3,17-dione (U.S. Pat. No. 2,867,630) is dehydrated to 6α-fluoroandrost-1,4,9(11)-triene-3,17-dione by means well known to those skilled in the art, see Steroid Reactions, C. Djerassi, Holden-Day, San Francisco, 1963 p. 238 & 239. The 16-methylene group is then added by the process of U.S. Pat. No. 4,416,821 to produce 6α-fluoro-16-methyleneandrosta-1,4,9(11)-triene-3,17-dione which is converted by the process of the present invention to 6α-fluoro-17α-hydroxy-16-methylenepregna-1,4,9(11)-triene-3,20-dione. The 21-hydroxy function of the corticoids is next introduced as described above followed by transformation of the 16-methylene group to a 16β-methyl group also described above to give 6α-fluoro-17α,21-dihydroxy-16β-methylpregna-1,4,9(11)-triene-3,20-dione 21-acetate which is acylated according to the procedure described in U.S. Pat. No. 4,154,748 (Examples 6 and 7) to produce 6α-fluoro-17α,21-dihydroxy-16β-methylpregna-1,4,9(11)-triene-3,20-dione 17,21-diacetate (U.S. Pat. No. 3,980,778, Example 6). 6α-Fluoro-17α,21-dihydroxy-16β-methylpregna-1,4,9(11)-triene-3,20-dione-17,21-diacetate is then converted to diflurasone diacetate by the process of U.S. Pat. No. 3,980,778 (Examples 7 and 8).

DEFINITIONS

The definitions and explanations below are for the terms as used throughout the entire patent application including both the specification and claims.

All temperatures are in degrees Centigrade.

TLC refers to thin-layer chromatography.

THF refers to tetrahydrofuran.

p-TSA refers to p-toluenesulfonic acid monohydrate.

Saline refers to an aqueous saturated sodium chloride solution.

NMR refers to nuclear (proton) magnetic resonance spectroscopy, chemical shifts are reported in ppm (δ) downfield from TMS.

TMS refers to tetramethylsilane.

When solvent pairs are used, the ratio of solvents used are volume/volume (v/v).

TEA refers to triethylamine.

LDA refers to lithium diisopropylamide.

Androstenedione refers to androst-4-ene-3,17-dione.

Dexamethasone refers to 9α-fluoro-11β,17α,21-trihydroxy-16α-methylpregna-1,4-diene-3,20-dione.

Betamethasone refers to 9α-fluoro-11β,17α,21-trihydroxy-16β-methylpregna-1,4-diene-3,20-dione.

Melengestrol acetate refers to 17α-hydroxy-6-methyl-16-methylenepregna-4,6-diene-3,20-dione 17-acetate.

Monolithium acetylide refers to $LiC_2H$ and complexed forms thereof.

A stabilizing amine is an amine (primary, secondary or tertiary), which when reacted with an organo lithium compound to form a lithium complex and subsequently reacted with acetylene forms a stabilized monolithium acetylide which will not significantly disproportionate at 0° and below and which is reactive towards 17-keto steroids.

Propylamine and butylamine include the isomers thereof namely npropyl and i-propylamine and n-butyl, i-butyl, s-butyl and t-butylamine.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

EXAMPLE 1

17α-Ethynyl-3,17β-dihydroxyandrosta-3,5-diene 3-methyl ether

THF is cooled to −40°. Acetylene is bubbled through for 65 minutes keeping the temperature at −40°. 3-Hydroxyandrosta-3,5-dien-17-one 3-methyl ether (1.00 g) is added and the mixture kept at −40° for another 10 minutes while acetylene bubbling continues. The acetylene is stopped and the pot temperature is kept at less than −35°.

In a separate flask diisopropylamine (1.27 ml) in THF is cooled in an ice bath. n-Butyllithium (1.6M), 5.64 ml)

is added dropwise to the amine mixture producing lithium diisopropylamide.

The lithium diisopropylamide mixture is then added dropwise to the steroid-acetylene mixture while maintaining the temperature at less than $-35°$. The mixture is stirred until TLC indicates the reaction is complete. The reaction mixture is poured into phosphate buffer (40 ml) and left overnight at $20°-25°$. The layers are separated. The aqueous layer is back extracted with ethyl acetate. The organic phases are combined, dried over sodium sulfate, filtered and the filtrate concentrated under reduced pressure to give the title compound which is crystallized from methanol.

EXAMPLE 2

17α-Ethynyl-17β-hydroxy-16β-methylandrosta-1,4,9(11)-trien-3-one

THF (50 ml) and diisopropylamine (40 ml) are mixed and cooled to $-20°$. Slowly n-butyl lithium (1.6M in hexane, 195 ml) is added with cooling maintaining the temperature in the range of $-22°$ to $-18°$. When addition is complete the lithium diisopropylamide is maintained at $-20°$.

THF (360 ml) is saturated with acetylene by bubbling acetylene thru the THF at $-20°$ to $-15°$. The acetylene saturated THF is then cooled to $-25°$.

The lithium diisopropylamide prepared above is added dropwise to the acetylene maintaining the reaction temperature less than $-10°$. When the lithium diisopropyl amide addition is complete, the monolithium acetylide is cooled to less than $-40°$.

16β-Methylandrosta-1,4,9(11)-triene-3,17-dione (U.S. Pat. No. 3,010,958, 20 g) is added in THF (60 ml) to the lithium acetylide at $-40°$. When the reaction is complete, acetone (24 ml) is added. The mixture is warmed while bubbling nitrogen thru the slurry to remove excess acetylene. Water (25 ml) is slowly added. Water (105 ml) is then added more quickly creating two phases which are separated. The aqueous phase is washed with THF (50 ml); the organic phases (pH is 9) are combined, washed with aqueous sulfuric acid and concentrated to 350 ml. Heptane (200 ml) is added, the mixture heated to 80° and held for 30 min. The mixture is cooled slowly to 30° and then to 18° for one hr. The mixture is filtered, the solid washed with heptane (20 ml) and then dried under reduced pressure with heat to give the title compound.

EXAMPLE 3

17α-Ethynyl-3,17β-dihydroxy-16-methyleneandrosta-3,5-diene 3-methyl ether

THF (400 ml) is cooled to $-40°$. Acetylene is sparged through the THF, with the temperature rising to $-28°$ and then over 0.5 hour dropping to $-36°$. Acetylene bubbling is continued another 0.5 hour. The mixture is cooled to $-43°$ and acetylene bubbled for an additional 0.5 hour. 3-Hydroxy-16-methyleneandrosta-3,5-dien-17-one 3-methyl ether (U.S. Pat. No. 4,416,821, 40.0 g) is added with stirring maintaining the $-50°$ cooling bath.

Diisopropylamine (44 ml) and THF (50 ml) are mixed and cooled to 8°. n-Butyl lithium (1.6M in hexane, 194 ml) is added at such a rate as to keep the exotherm below 25°. When the addition is complete, the lithium diisopropylamide mixture is transferred via a cannula to an addition funnel and then added dropwise to the steroid-acetylene mixture while maintaining the reaction temperature $<-38°$ (bath temperature was $-50°$).

When addition is complete (65 minutes) TLC indicates the reaction is approximately 98% complete. The reaction mixture is added slowly into saline/water (1 l, 1/1) and stirred. The layers are separated. The aqueous layer is extracted with ethyl acetate (200 ml). The organic phases are combined, washed with saline, dried over sodium sulfate after addition of triethylamine (1 ml) and concentrated under reduced pressure to a volume of about 80 ml. Methanol (200 ml) and triethylamine (1 ml) are added and the mixture concentrated under reduced pressure to about 100 ml. Methanol (200 ml) is added and the mixture again concentrated to about 100 ml. The mixture is filtered, the solids washed with cold methanol to give the title compound.

EXAMPLE 4

17α-Ethynyl-3,17β-dihydroxy-16-methyleneandrosta-3,5-diene 3-methyl ether

Dry THF (250 ml) previously cooled to $-10°$ is sparged with acetylene until saturated.

Dry THF (50 ml) and diisopropylamine (44 ml) are cooled to $-20°$. n-Butyl lithium (1.6M, 194 ml) is added to the amine/THF mixture producing lithium diisopropylamide. The lithium diisopropyl amide is slowly added to the acetylene maintaining the temperature at about $-20°$ thereby producing monolithium acetylide.

3-Methoxy-16-methyleneandrosta-3,5-dien-17-one (U.S. Pat. No. 4,416,821, 50.0 g) in THF (250 ml) is added dropwise over a period of 30 min. to the monolithium acetylide maintaining the temperature at about $-20°$. TLC indicates the reaction is complete after about 15 minutes. The reaction mixture is then added to water (500 ml) containing sodium chloride (75 g) via a drop funnel and stirred 10 min. The two phases are separated and the aqueous phase backextracted with ethyl acetate (200 ml). The ethyl acetate back-wash is combined with the organic phase and the aqueous phase is discarded. The organic phase is washed with water (500 ml) containing sodium chloride (75 g), dried and concentrated under reduced pressure at less than 30° to a volume of about 175 ml. Methanol (200 ml), water (30 ml) and TEA (1 ml) are added. The mixture is concentrated to about 200 ml by distillation, cooled to 10°, stirred 10 min. and filtered. The solids are washed twice with methanol ($2 \times 50$ ml) containing 15% water. The solids are dried overnight at 50° under reduced pressure to give the title compound (first crop). The mother liquor is concentrated under reduced pressure at less than 35° to one-half its volume, cooled to 10°, stirred 5 min. and filtered. The solids are washed twice with cold methanol ($2 \times 20$ ml) containing 15% water, dried overnight at 50° under reduced to give a second crop of the title compound.

EXAMPLE 5

17α-Ethynyl-17β-hydroxy-6β-(N-phenyl-N-ethylaminomethyl)-16-methyleneandrosta-4-en-3-one 17α-Ethynyl-3,17β-dihydroxy-16-methyleneandrosta-3,5-diene 3-methyl ether (Example 3, 5 g), ethyl aniline (2.05 ml), THF (37.5 ml), and formaldehyde (37%, 1.33 g) were mixed. p-TSA (140 mg) was added and the mixture stirred overnight at 20°-25°. TLC showed the reaction to be complete. Water (100 ml) was added, the mixture filtered, the solids washed twice with water/THF; 2/1, the solid material was dried under nitrogen for 5 hours to give the title compound. NMR (CDCl₃) 0.85, 1.31, 2.52, 5.23, 5.82, 6.7 and 7.2δ.

EXAMPLE 6

17α-Ethynyl-17β-hydroxy-6,16-dimethyleneandrosta-4-en-3-one

17α-Ethynyl-17β-hydroxy-6β-(N-phenyl-N-ethylaminomethyl)-16-methyleneandrosta-4-en-3-one (Example 5) in THF (20 ml) are mixed. Degassed hydrochloric acid (6N, 55 ml plus 20 ml THF) are added. The mixture is stirred overnight at 20°–25° under nitrogen, at which time TLC shows the reaction to be complete. Water (110 ml) is added, the mixture filtered, the solids washed with 10% hydrochloric acid, twice with water, once with 5% sodium bicarbonate, and three times with water to neutrality. Solids were then dried under nitrogen overnight to give the title compound.

EXAMPLE 17

17α-Acetyl-17β-hydroxy-6,16-dimethyleneandrosta-4-en-3-one

Mercuric oxide red (0.32 g) was mixed with sulfuric acid/water (sulfuric acid, 0.4 ml; water, 6.0 ml) and let stand overnight. 17α-Ethynyl-17β-hydroxy-6,16-dimethyleneandrosta-4-en-3-one (Example 6, 5.0 g) is mixed with THF (15 ml). The mercuric sulfate solution is added the reaction heated to 41°–49° over a period of 6 hrs at which time TLC indicates the reaction is completed. Sodium carbonate (0.79 g) in water (10 ml) is added and the mixture stirred for 5 min. Celite (5 g) is added and the mixture stirred ½ hr at 20°–25°. The mixture is filtered through Celite (5 g), the solids washed with methanol/THF; 1/1 (2×10 ml) and once with THF (10 ml), followed by methylene chloride (10 ml). The filtrate and washings are concentrated under reduced pressure to about 35 ml, at which point crystals begin forming. Methanol (50 ml) is added and the mixture again concentrated under reduced pressure and permitted to sit overnight at 20°–25° under nitrogen atmosphere. Water (500 ml) is added, slowly at first, with stirring over a period of 15 min. The mixture is filtered, the solids washed with water (3×20 ml), and hexane (2×10 ml). The solids were dried under nitrogen to give the title compound.

EXAMPLE 8

6-Methylene-16-(phenylsulfinylmethyl)pregna-4,16-diene-3,20-dione

17α-Acetyl-17β-hydroxy-6,16-dimethyleneandrosta-4-en-3-one (Example 7, 8.0 g) is dissolved in methylene chloride (66 ml) and cooled to −20°. Trimethylamine (2.56 ml) at −20° and methylene chloride (5 ml) are mixed and the trimethylamine mixture transferred by syringe to the steroid solution. The cold steroid solution was added phenylsulfonylchloride (1.0 equivalent) by a syringe pump over 1 hr. TLC shows the reaction approximately 80–85% complete. Phenylsulfonylchloride (0.25 equivalent) was added over approximately 10 min., TLC showing the reaction to be approximately 95% complete. Phenylsulfonylchloride (0.10 equivalent) was then added for a total of 1.35 equivalence, at which time TLC shows the reaction to be complete. Hydrochloric acid (10%, 40 ml) was added all at once, the temperature now being 7°, and the mixture stirred for about 10 min. The phases are separated. The aqueous portion is back-extracted with methylene chloride (10 ml). The organic extracts are washed with phosphate buffer (25 ml) and back-extracted with methylene chloride (10 ml). The organic extracts are combined, dried over sodium sulfate overnight at 20°–25°. This mixture is filtered and the filtrate concentrated under reduced pressure to an oil, which is the title compound.

EXAMPLE 9

17α-Hydroxy-6,16-dimethylenepregn-4-ene-3,20-dione

6-Methylene-16-phenylsulfonylmethylpregna-4,16-diene-3,20-dione (Example 8, 2.0 g) is placed in a 30-ml vial under nitrogen. Toluene (20 ml), methanol (2.89 ml), TEA (0.181 ml) and trimethylphosphite 1.02 ml) are added. After 1 hr at 20°–25°, the sealed vial was plunged into a hot oil bath with a bath temperature of 90° which is stirred at 90° for 4 hrs, at which time TLC shows the reaction to be essentially complete. The reaction mixture is transferred to a separatory funnel and water (10 ml) is added. Ethyl acetate (10 ml) is added to the organic mixture, which is washed with water (2×10 ml). The aqueous portion is back-extracted with toluene/ethyl acetate: 1/1. After the phases are separated, the organic phase is filtered through sodium sulfate and the filtrate is concentrated under reduced pressure to a volume of about 8 ml. This concentrate is permitted to sit at 20°–25° for approximately ½ hr. The resulting crystals are washed down into a flask with toluene (2 ml) and cooled to 5° for 2 hrs, then to −20° for 48 hrs. The crystals were collected with toluene (−20°), then with hexane three times and dried under nitrogen to yield the title compound.

EXAMPLE 10

17α-Hydroxy-6-methyl-16-methylenepregna-4,6-diene-3,20-dione 17-acetate (Melengestrol acetate)

17α-Hydroxy-6,16-dimethylenepregna-4-ene-3,20-dione (Example 9, 50 mg) is slurried in toluene (1.5 ml). Acetic anhydride (95 μl, 7 equivalents) and p-TSA/water (8 mg, 0.3 equivalents) are added. The reaction vessel is capped and heated to 85° for 3 hrs 20 min., then pulled from the heat, cooled and TLC shows the reaction is approximately 70% complete. The reaction mixture is heated for an additional 3 hrs, permitted to stand at 20°–25° overnight, at which time TLC shows the reaction is complete. Hydrochloric acid (6N, 200 μl) is added and the mixture stirred 1 hr at 20°–25°. On work-up, the title compound is obtained.

EXAMPLE 11

17α-Hydroxy-16-methylenepregn-4-ene-3,20-dione (17α-hydroxy-16-methyleneprogesterone)

Following the general procedure of Example 7–9 and making noncritical variations but starting with 17α-ethynyl-3,17β-dihydroxy-16-methyleneandrosta-3,5-diene 3-methyl ether (Example 3) the title compound is obtained.

EXAMPLE 12

17α-Ethynyl-3,17β-dihydroxy-16-methyleneandrost-3,5-diene 3-methyl ester

Dry THF (50 l) is cooled to −20° and acetylene (2.7 kg) is dissolved in the THF.

In a separate tank diisopropylamine (8.8 l) is dissolved in dry THF (10 l) and cooled to −20°. n-Butyllithium (1.6M in hexane, 38.8 l) is added slowly to the amine at −20±5°.

The lithium-amine mixture is added slowly to the acetylene solution at −20±5°.

3-Methoxy-16-methyleneandrost-3,5-dien-17-one (10 kg) in THF (50 l) is added to the reaction mixture at or below −20° and stirred for 20 min to give the title compound.

EXAMPLE 13

17α-Ethynyl-17β-hydroxy-16β-methylandrosta-1,4,9(11)-trien-3-one

Dry THF (5 l) is cooled to −20° and acetylene (0.27 kg) is dissolved in the THF at −20°. Diisopropylamine (880 ml) is added to the acetylene/THF solution. n-Butyllithium (1.6M, 3.88 l) is added to the mixture maintaining the temperature at −20° and stirred for 30 min. The ketone is then added, and reacted as in Example 12 to give the title compound.

EXAMPLE 14

17α-Ethynyl-17β-hydroxy-16β-methylandrosta-1,4,9(11)-trien-3-one

THF (315 ml) and diisopropylamine (122 g) are mixed and cooled to −30°. n-Butyllithium (480 g) is added slowly to form LDA maintaining the temperature at −20±1°.

THF (1.36 l) is cooled to −20° and acetylene (100 g) is dissolved in the THF using a nitrogen sweep (for safety reasons). The mixture is cooled to less than −25° and the LDA mixture is added slowly keeping the temperature less than −20°. The entire monolithium acetylide mixture is cooled to −45°.

16β-Methylandrosta-1,4,9(11)-triene-3,17-dione (70 g) is dissolved in THF (260 ml) and cooled to 20°-22°.

The steroid mixture is added to the monolithium acetylide keeping the pot temperature at −40°, the addition is complete in 10 min or less. When the reaction is complete (about 10 min at −40°) the reaction mixture is quenched with acetone (106 ml) in water (35 ml) keeping the temperature at less than −35°. The mixture is sparged with nitrogen. Water (480 ml) is added and the mixture warmed to 45°. The mixture is degassed under reduced pressure for 30 min monitoring the acetylene by GLC and then cooled to about 25°.

The reaction mixture is worked up by means well known to those skilled in the art.

We claim:

1. A process to prepare monolithium acetylide which comprises
   (1) dissolving acetylene in a dry solvent
   (2) contacting a stabilizing mono-amine with an organo-lithium compound from about 0° to about −40°
   (3) contacting the product of step (2) with the solution of step (1) from about 0° to about −40°.

2. A process according to claim 1 where the dry solvent is selected from the group consisting of THF, dioxane, diethyl ether, t-butylmethyl ether and dimethoxyethane.

3. A process according to claim 1 where the stabilizing amine is selected from the group consisting of ethylamine, propylamine, butylamine, diisopropylethylamine, triethylamine, diisopropylamine, diethylamine, dicyclohexylamine, hexamethyldisilazane.

4. A process according to claim 1 where the organo-lithium compound is selected from the group consisting of phenyllithium, n-butyllithium or methyllithium.

5. A process according to claim 1 where the temperature is about −20° or less.

6. A process to prepare monolithium acetylide which comprises
   (1) dissolving acetylene in a dry solvent,
   (2) contacting a stabilizing mono-amine with the solution of step (1), and
   (3) contacting an organo-lithium compound with the mixture of step (2) from about 0° to about −40°.

7. A process according to claim 6 where the dry solvent is selected from the group consisting of THF, dioxane, diethyl ether, t-butylmethyl ether and dimethoxyethane.

8. A process according to claim 6 where the stabilizing amine is selected from the group consisting of ethylamine, propylamine, butylamine, diisopropylethylamine, triethylamine, diisopropylamine, diethylamine, dicyclohexylamine, hexamethyldisilazane.

9. A process according to claim 6 where the organo-lithium compound is selected from the group consisting of phenyllithium, n-butyllithium or methyllithium.

10. A process according to claim 6 where the temperature is about −20° or less.

11. A process to prepare monolithium acetylide and a 17α-ethynyl-17β-hydroxy steroid which comprises
    (1) dissolving acetylene in a dry solvent,
    (2) contacting a 17-keto steroid with the mixture of step (1),
    (3) contacting a stabilizing mono-amine with an organo-lithium compound at about 0° or less, and
    (4) contacting the mixture of step (3) with the mixture of step (2) from about 0° to about −40°.

12. A process according to claim 11 where the dry solvent is selected from the group consisting of THF, dioxane, diethyl ether, t-butylmethyl ether and dimethoxyethane.

13. A process according to claim 11 where the stabilizing amine is selected from the group consisting of ethylamine, propylamine, butylamine, diisopropylethylamine, triethylamine, diisopropylamine, diethylamine, dicyclohexylamine, hexamethyldisilazane.

14. A process according to claim 11 where the organo-lithium compound is selected from the group consisting of phenyllithium, n-butyllithium or methyllithium.

15. A process according to claim 11 where the temperature is about −20° or less.

16. A process according to claim 11 where the 17-keto steroid is a 16-methylene-17-keto steroid.

17. A process according to claim 16 where the 17-keto steroid is selected from the group consisting of 16β-methyl-17-keto, and 16α-methyl-17-keto steroids.

* * * * *